US008358134B1

(12) United States Patent
Hoyt

(10) Patent No.: US 8,358,134 B1
(45) Date of Patent: Jan. 22, 2013

(54) MARKER FOR PIPELINE APPARATUS AND METHOD

(75) Inventor: Philip M. Hoyt, Murray, UT (US)

(73) Assignee: Pure Technologies Ltd., Calgary (CA)

( * ) Notice: Subject to any disclaimer, the term of this patent is extended or adjusted under 35 U.S.C. 154(b) by 511 days.

(21) Appl. No.: 12/541,076

(22) Filed: Aug. 13, 2009

Related U.S. Application Data

(63) Continuation-in-part of application No. 12/258,372, filed on Oct. 24, 2008, now abandoned.

(51) Int. Cl.
*G01V 3/08* (2006.01)
(52) U.S. Cl. .................................... 324/326; 324/332
(58) Field of Classification Search .................. 324/326, 324/332
See application file for complete search history.

(56) References Cited

U.S. PATENT DOCUMENTS

| | | | |
|---|---|---|---|
| 2,860,313 A * | 11/1958 | Israel | 336/110 |
| 3,335,383 A | 8/1967 | Jorden | |
| 3,373,391 A | 3/1968 | Bohn et al. | |
| 4,075,601 A | 2/1978 | Flournoy et al. | |
| 4,091,322 A * | 5/1978 | Stankoff | 324/329 |
| 4,253,167 A | 2/1981 | Flournoy | |
| 4,522,790 A | 6/1985 | Dantzig et al. | |
| 4,587,509 A | 5/1986 | Pitt et al. | |
| 4,692,703 A | 9/1987 | Extance et al. | |
| 4,857,851 A | 8/1989 | Anderson et al. | |
| 5,942,895 A | 8/1999 | Popovic et al. | |
| 6,023,986 A | 2/2000 | Smith et al. | |
| 6,243,657 B1 | 6/2001 | Tuck et al. | |
| 6,501,268 B1 | 12/2002 | Edelstein et al. | |
| 6,529,169 B2 | 3/2003 | Justice | |
| 6,545,462 B2 | 4/2003 | Schott et al. | |
| 6,707,183 B2 | 3/2004 | Breynaert et al. | |
| 6,720,855 B2 | 4/2004 | Vicci | |
| 6,724,652 B2 | 4/2004 | Deak | |
| 6,816,110 B1 | 11/2004 | Liu | |
| 6,914,805 B2 | 7/2005 | Witcraft et al. | |
| 7,009,399 B2 * | 3/2006 | Olsson et al. | 324/326 |
| 7,015,874 B2 | 3/2006 | Ikramov et al. | |
| 7,112,957 B2 | 9/2006 | Bicking | |
| 7,113,148 B2 | 9/2006 | Lan et al. | |
| 7,129,904 B2 | 10/2006 | Chen | |
| 7,167,140 B2 | 1/2007 | Kato et al. | |
| 7,209,090 B2 | 4/2007 | Hall et al. | |
| 2009/0243601 A1 * | 10/2009 | Feldtkeller | 324/207.26 |

* cited by examiner

*Primary Examiner* — Bot Ledynh
(74) *Attorney, Agent, or Firm* — Warren M. Pate, LLC

(57) ABSTRACT

Defects in a pipeline may be detected by an in-line inspection tool passing therethrough. However, as the tool travels through the pipeline, errors associated with certain onboard components may accumulate. These errors may reduce the accuracy with which the locations of detected defects can be determined. Accordingly, markers may be positioned at various locations along the pipeline. Each marker may include a radio receiver to receive signal transmitted by an in-line tool passing thereby and one or more magnetic flux detection systems that may detect a magnetic field emanating from the in-line tool. The radio receiver may include an antenna comprising two or more coils connected in series and positioned side-by-side. The flux detection system may include one or more flux concentrators to amplify the strength of the magnetic field. Signals received through the antenna or flux detection system may be used to correct any errors associated with the onboard components charting the progression of the in-line tool through the pipeline.

8 Claims, 12 Drawing Sheets

MARKER FOR PIPELINE APPARATUS AND METHOD

RELATED APPLICATIONS

This application is a continuation-in-part of U.S. patent application Ser. No. 12/258,372 filed Oct. 24, 2008 now abandoned, which is hereby incorporated by reference.

FIELD OF THE INVENTION

This invention relates to pipeline inspection tools and systems, and more particularly to apparatus and methods for above ground markers for use in connection with in-line tools.

BACKGROUND OF THE INVENTION

Oil, petroleum products, natural gas, hazardous liquids, and the like are often transported using pipelines. The majority of these pipelines are constructed from steel pipe. Once installed, a pipeline will inevitably corrode or otherwise degrade. Proper pipeline management requires identification, monitoring, and repair of defects and vulnerabilities of the pipeline. For example, information collected about the condition of a pipeline may be used to determine safe operating pressures, facilitate repair, schedule replacement, and the like.

Typical defects of a pipeline may include corrosion, gouges, dents, and the like. Corrosion may cause pitting or general wall loss, thereby lowering the maximum operating pressure of the pipeline. Vulnerabilities may also include curvature and bending anomalies, which may lead to buckling, and combined stress and chemical or biological action such as stress corrosion cracking. Without detection and preemptive action, all such defects and vulnerabilities may lead to pipeline failure.

Information on the condition of a pipeline is often collected using an in-line tool. For example, an in-line inspection tool typically uses sensors to collect information about a pipeline as it travels therethrough. In the past, in-line inspection tools have used technologies such as magnetic flux leakage or ultrasonic testing to determine the condition of a pipeline wall. Flaws in ferromagnetic pipe can be detected by the perturbations they cause in a magnetic field applied to the wall of a pipeline. Flaws can also be detected by ultrasonic wall thickness measurement.

To collect useful data, the location and orientation of an in-line tool within a pipeline must be accurately known. When the location and orientation of an in-line tool are accurately known, then the locations of defects detected by the in-line tool can be accurately known. Accordingly, in-line tools often include components dedicated to determining location and orientation.

As an in-line tool travels through a pipeline, errors associated with the components measuring location may accumulate. These errors may reduce the accuracy with which an operator of the in-line tool can determine the locations of defects detected by the tool. Accordingly, markers are commonly placed outside the pipe at points with known locations. These markers communicate with the inspection tool to provide additional reference points that can be used to correct any errors associated with the onboard measuring components of an in-line tool.

Markers commonly locate in-line tools by recognizing the presence of the magnetic field emanating from the inspection system onboard the tool. However, this field is often weak and may be missed or misread by existing markers. Moreover, stray magnetic fields from extraneous sources such as electric power lines often appear the same as in-line tools to existing markers. Some markers include components intended to minimize the effects of stray magnetic fields. Such components make the markers large and typically do not work well.

Markers also commonly recognize the signal from transmitters onboard the in-line tool. Receivers are large and bulky and consist of a coil that is long and that makes the entire marker long. Attempts to make the receiving coil smaller have resulted in decreased sensitivity of the receiver and in markers that perform poorly.

Existing markers are not reliable because they often miss magnetic signals from in-line tools, they do not adequately discriminate between magnetic fields emanating from an in-line tool and stray magnetic fields, and they do not clearly recognize transmitted signals from in-line tools. Moreover, markers must be transported to reference locations but existing markers are large, bulky and difficult to transport. Accordingly, what is needed is a system and method that will provide required reference points more reliably and in a more compact package.

SUMMARY

A method in accordance with the present invention may begin with the selection of a pipeline to be inspected. Once the pipeline is selected, an in-line tool may be inserted therein. The in-line tool may have various sensors to inspect the physical condition of the pipeline as it travels therethrough.

As an in-line tool travels through a pipeline, errors associated with the onboard components measuring location may accumulate. These errors may reduce the accuracy with which an operator of the in-line tool can determine the locations of defects detected by the tool. To combat these errors and provide additional location reference points, the operator may select one or more locations proximate the pipeline. At each such location, the operator may position a marker. Deploying markers to the various locations may be accomplished in any suitable manner. In certain embodiments, an operator may select an installer. The installer may transport the one or more markers to their appropriate locations and deposit them. Depending on the terrain proximate the pipeline and any regulations applicable thereto, the installer may be required to transport the markers to the desired locations on foot.

In selected embodiments, a marker may include a power source, a receiver for a global position positioning system, and a radio receiver. The radio receiver may receive signal transmitted by an in-line tool passing thereby. Various characteristics of the signal or the data communicated by the signal may be recorded by the marker. Later, when the data collected by an in-line tool is analyzed, the characteristics of the signal, data communicated by the signal, or some combination thereof may be used to determine the location of the marker and to correct any errors associated with the onboard components that charted the progression of the in-line tool through the pipeline.

In certain embodiments, the radio receiver of a marker in accordance with the present invention may include an antenna comprising one or more coils. The coils may be positioned so as to be non-coaxial. For example, each coil may comprise a conductor coiled around a central axis. The central axis of one coil may be radially spaced from, and parallel to, the central axis or axes of the other coil or coils.

In such an embodiment, the two or more coils may comprise one continuous winding. The winding may begin with a first coil, and then progress to the second coil, etc. The second coil, as well as any other subsequent coils, may be wound in the same direction as the first coil. Moreover, the various coils may be connected in series. Accordingly, electrical currents induced in the coils may flow in the same direction, reinforcing the total output current. Thus, antennas in accordance with the present invention may provide the desired sensitivity in a compact envelope.

The compact envelope of an antenna in accordance with the present invention may facilitate deployment of a corresponding marker. That is, the compact size may permit multiple markers to be easily carried by foot (e.g., in an installer's backpack) to desired locations along a pipeline.

In certain embodiments, a marker in accordance with the present invention may include one or more magnetic flux detection systems. These flux detection systems may be configured to sense the magnets of an in-line tool (e.g., an in-line inspection tool using magnetic flux leakage to detect defects in a pipeline). Each flux detection system may include one or more concentrators enabling the marker to locate an in-line tool much more readily.

An in-line tool may be detected by the presence of any component (e.g., axial, radial, circumferential) of the flux field generated thereby. Other electromagnetic phenomena exist that could produce a false indication of the presence of the in-line tool but they do not typically have the same signal characteristics in each component as the components of the flux field emanating from the in-line tool. Accordingly, a marker may discriminate between the magnetic field of an in-line tool and some other electromagnetic phenomenon by searching the signals received by the flux detection systems for the characteristic shapes corresponding to the components of the magnetic field. The marker may require that the signals have those characteristic shapes before sending an indication that the in-line tool has passed thereby.

For added accuracy in discrimination, a system may search multiple signals for the corresponding shapes and only send an indication that the in-line tool has passed when those multiple signals all simultaneously display their corresponding characteristic shapes. In selected embodiments, these multiple signals further may include any combination of the components of a magnetic field and the radio frequency signal received by an antenna.

Markers may be placed in any location proximate a pipeline. They may be above ground, directly adjacent to an exposed section of pipeline, proximate to a subsea pipeline by attachment to the pipe or supported by a flotation device, or any other placement location or means. Moreover, a marker may be moved along the pipeline to locate an in-line tool that may be stopped or whose location is otherwise desired.

BRIEF DESCRIPTION OF THE DRAWINGS

The foregoing features of the present invention will become more fully apparent from the following description and appended claims, taken in conjunction with the accompanying drawings. Understanding that these drawings depict only typical embodiments of the invention and are, therefore, not to be considered limiting of its scope, the invention will be described with additional specificity and detail through use of the accompanying drawings in which:

DETAILED DESCRIPTION

Figure 1:
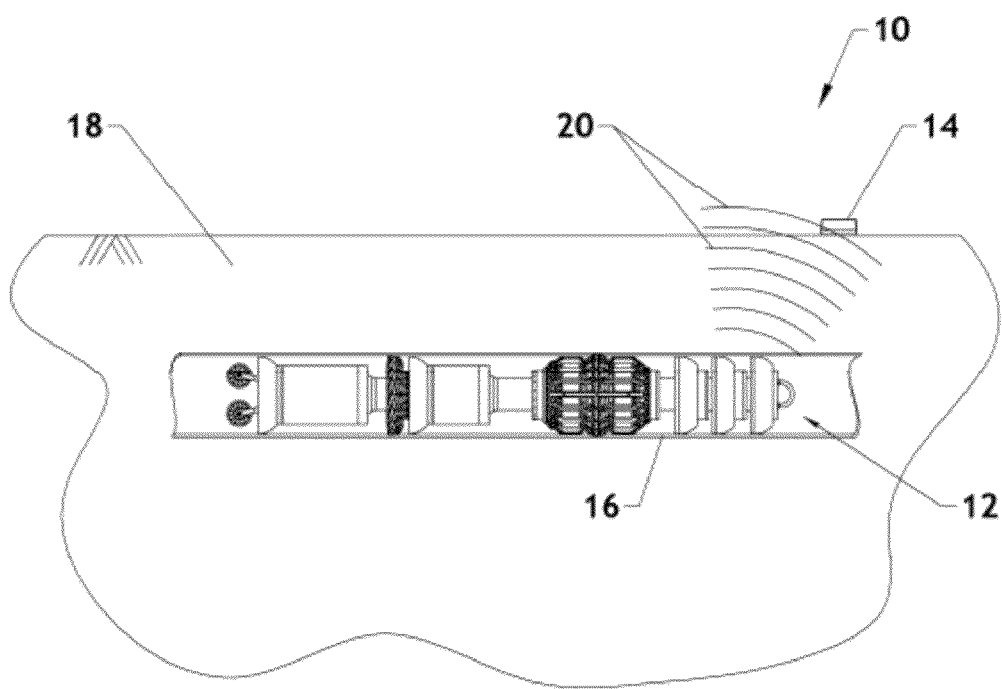
FIG. 1 is a schematic diagram illustrating one embodiment of a pipeline inspection system in accordance with the present invention.

It will be readily understood that the components of the present invention, as generally described and illustrated in the drawings herein, could be arranged and designed in a wide variety of different configurations. Thus, the following more detailed description of the embodiments of the system and method of the present invention, as represented in the drawings, is not intended to limit the scope of the invention, as claimed, but is merely representative of various embodiments of the invention. The illustrated embodiments of the invention will be best understood by reference to the drawings, wherein like parts are designated by like numerals throughout.

Referring to FIG. 1, in selected embodiments, a pipeline system 10 in accordance with the present invention may include an in-line tool 12 and one or more markers 14. An in-line tool 12 may be sized and configured to travel through a pipeline 16. Markers 14 may be positioned at known locations proximate the pipeline 16. As an in-line tool 12 passes by a marker 14, the two devices may interact. This interaction may provide a reference point to correct any errors or drift associated with the onboard measuring components of the in-line tool 12.

In-line tools 12 in accordance with the present invention may have any suitable configuration. In selected embodiments, an in-line tool 12 may comprise an in-line inspection tool 12 configured to detect defects in a pipeline 16 as it travels therethrough. Selected in-line inspection tools 12 that may be suitable are disclosed in U.S. patent application Ser. No. 12/478,137 filed Jun. 4, 2009, U.S. patent application Ser. No. 12/403,754 filed Mar. 13, 2009, and U.S. patent application Ser. No. 12/366,606 filed Feb. 5, 2009, each of which is hereby incorporated by reference.

An in-line tool 12 may interact with a marker 14 in any suitable manner. In selected embodiments, the interaction may accommodate the physical barriers separating the in-line tool 12 from the marker 14. For example, in certain embodiments, a pipeline 16 being inspected may be buried underground. Accordingly, a quantity of earth 18 may separate an in-line tool 12 from a marker 14. In such embodiments, interaction between the in-line tool 12 and marker 14 may be accomplished using radio waves 20. For example, in-line tools 12 and markers 14 may interact using electromagnetic radiation of extremely low frequency (ELF) to super low frequency (SLF) or International Telecommunication Union (ITU) bands 1 and 2.

The direction of communication between an in-line tool 12 and a marker 14 may vary between embodiments. In selected embodiments, communication may be directed exclusively from an in-line tool 12 to a marker 14. Accordingly, in such embodiments, an in-line tool 12 may include a transmitter, while a marker 14 includes a receiver.

Alternatively, communication may be directed exclusively from a marker 14 to an in-line tool 12. In such embodiments, a marker 14 may include a transmitter, while an in-line tool 12 includes a receiver. In still other embodiments, communication between an in-line tool 12 and a marker 14 may be two way. Accordingly, in such embodiments, both an in-line tool 12 and a marker 14 may include a transmitter and receiver.

Data passed between an in-line tool 12 and a marker 14 may vary between embodiments. In general, the data may have any form or content necessary to provide the desired reference points or corrections for any errors or drift associated with the onboard measuring components of the in-line tool 12. In selected embodiments, the data may simply be the presence of the in-line tool and location information may be correlated by reference to the time at which the in-line tool passes the marker. In other embodiments, the data may include time stamps, location information, identification information, or the like.

Figure 2:
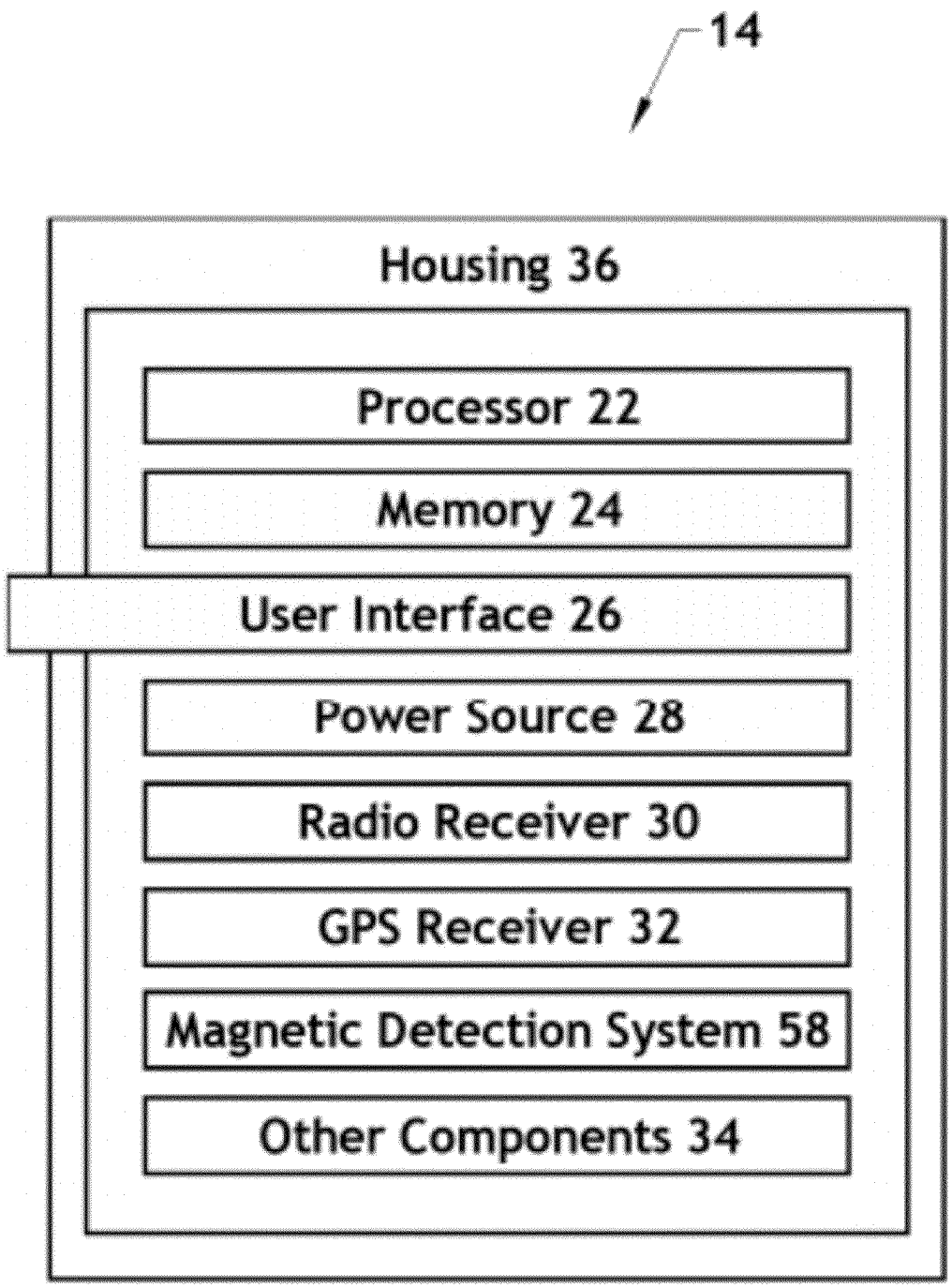
FIG. 2 is a schematic block diagram of one embodiment of a marker in accordance with the present invention.

Referring to FIG. 2, in selected embodiments, a marker 14 in accordance with the present invention may include a processor 22, memory 24, user interface 26, power source 28, radio receiver 30, global positioning system (GPS) receiver 32, a magnetic flux detection system 58 and other components 34 as desired or necessary. A marker 14 may also include a housing 36 containing and protecting the various components of the marker 14.

In operation, a processor 22 may execute one or more programs stored in memory 24. Through such programs, a processor 22 may control the various components of the marker 14. For example, a processor 22 may control which frequencies or channels are monitored by the radio receiver 30, what data is recorded in memory 24, etc.

A processor 22 may also recognize coding in the signal transmitted from the in-line tool 12, thereby eliminating false indications from sources other than the in-line tool 12. Alternatively, a processor 22 may provide coding in a signal transmitted from the marker 14 to the in-line tool 12.

A user interface 26 in accordance with the present invention may provide a user (e.g., the person positioning or installing a marker 14) with one or more input mechanisms through which the user may control various aspects of the marker 14. A user interface 26 may also provide mechanisms for exporting data stored within memory 24. For example, a user interface 26 may permit a user to turn the marker 14 on or off, change the frequency or channel being monitored by the radio receiver 30, etc.

A user interface 26 may also include screens, ports, or the like for displaying or outputting data to a user. In selected embodiments, a user interface 26 may connect to the rest of a marker 14 through a hard wired connector. Alternatively, a user interface 26 may be contained within the housing 36 of the marker 14 and include a hard wired connection (e.g., a selectively releasable hard wired connection) to external devices that download information from the marker 14 or have a transmitter and receiver communication link enabling remote communication for data transfer, activation of remote signaling devices, etc.

In selected embodiments, a user interface 26 may be contained completely within the housing 36 of the marker 14. In such embodiments, a user may open the housing 36 to access or utilize the user interface 26. In other embodiments, a portion of the user interface 26 may extend to the exterior of the housing 36, permitting a user to manipulate the user interface 26 without opening the housing 36.

In certain embodiments, a power source 28 in accordance with the present invention may comprise a battery. The battery may have a capacity selected to meet the electrical power requirements of the marker 14 for a specified period of time. In selected embodiments, this specified period of time may permit a marker 14 to be used multiple times before requiring a recharge or change of battery.

A marker 14 may include a GPS receiver 32. The GPS receiver 32 may assist in accurately determining the position of the marker 14. In selected embodiments, position information collected by a GPS receiver 32 may be stored in memory 24. In certain embodiments, a GPS receiver 32 may be activated via a user interface 26 once a marker 14 has been placed in the desired location by the user. The location information produced by a GPS receiver 32 may be stored once after positioning the marker 14. Alternatively, the location information produced by the GPS receiver 32 may be stored multiple times or continuously.

Figure 3:
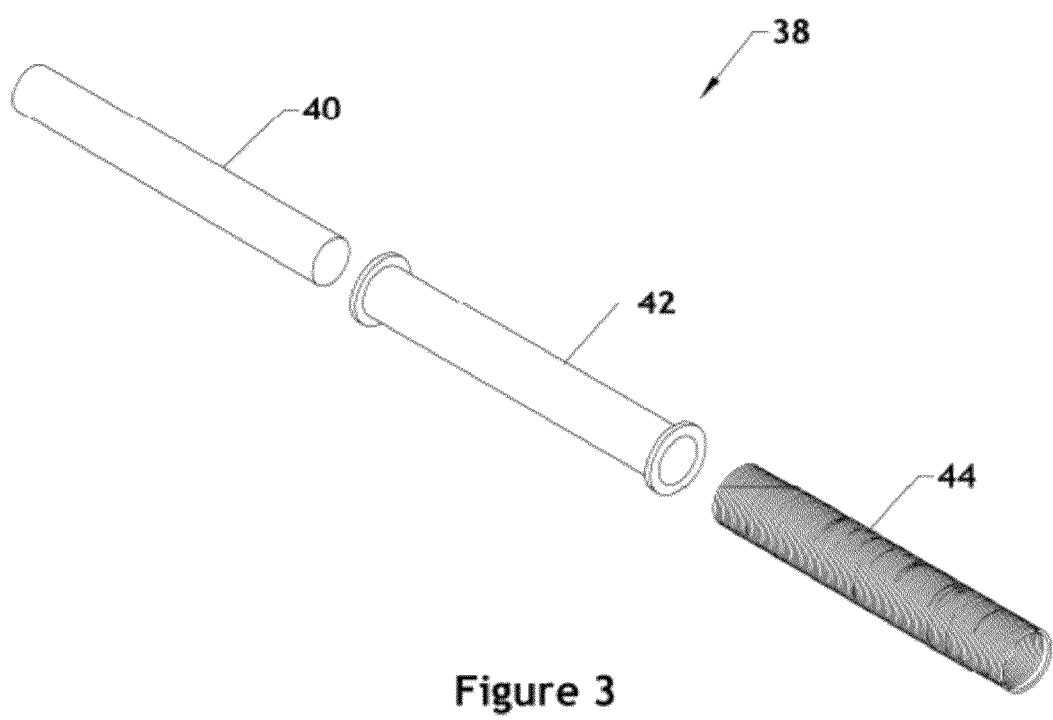
FIG. 3 is an exploded perspective view of one embodiment of an antenna in accordance with the present invention.
Figure 4:
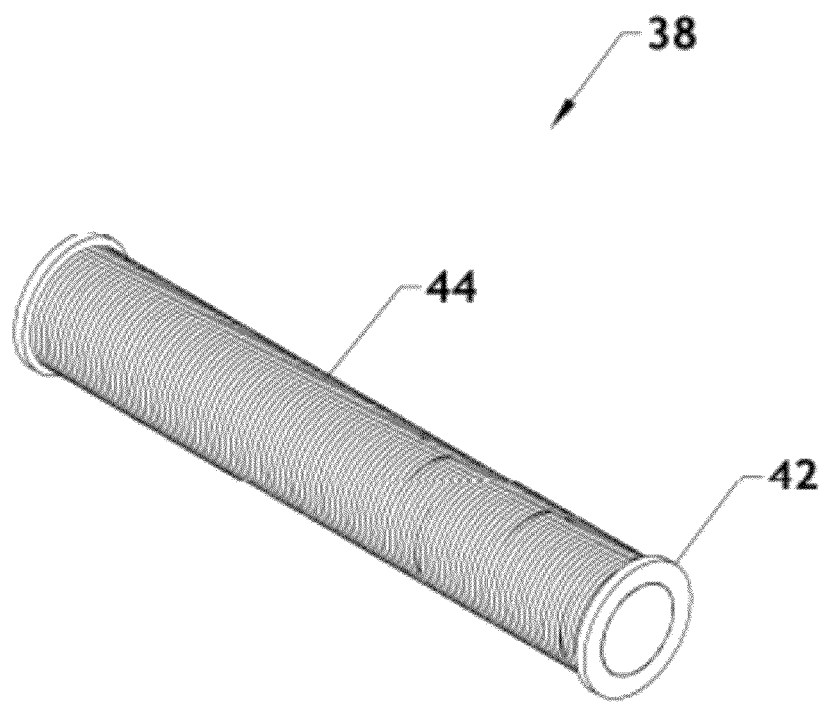
FIG. 4 is an assembled perspective view of the antenna of FIG. 3.

Referring to FIGS. 3 and 4, a radio receiver 30 or transmitter may include an antenna 38. Such an antenna 38 may be shaped and sized to receive or transmit any desired frequencies. In selected embodiments, an antenna 38 may be configured to receive extremely low frequency (ELF) to super low frequency (SLF) bands of radio frequency (RF) electromagnetic radiation, or International Telecommunication Union (ITU) bands 1 and 2. In-line tools 12 may transmit at such frequencies to maximize penetration through the wall of a pipeline 16 and through surrounding material such as earth 18. By receiving such frequencies, a marker 14 may track an in-line tool 12.

In selected embodiments, an antenna 38 in accordance with the present invention may comprise a core 40, coil form 42, and coil 44. A core 40 may comprise a magnetically permeable material (e.g., ferrite) or open space. A coil form 42 may secure or hold in place the electrically conductive wire forming the coil 44. When a coil 44 is acting as a receiver, each turn of the coil 44 may collect electromagnetic energy and pass it along as an electric current. A coil 44 may become more sensitive by increasing the number of turns in the coil 44.

Figure 5:
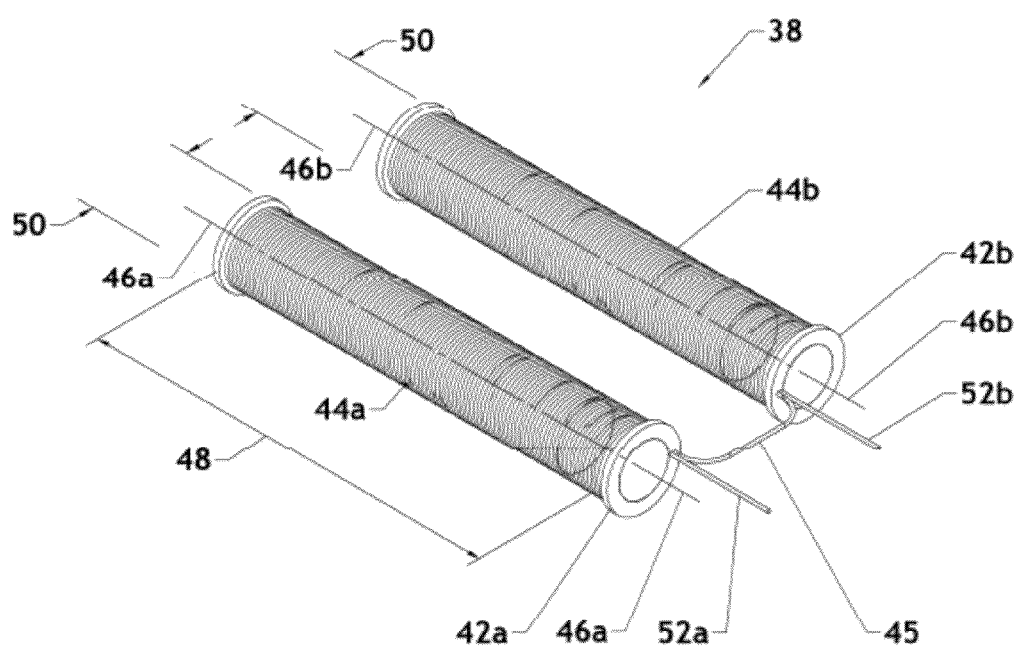
FIG. 5 is a perspective view of a multi-coil embodiment of an antenna in accordance with the present invention.

Referring to FIG. 5, in selected embodiments, an antenna 38 may include two or more coils 44a, 44b positioned so as to be non-coaxial. For example, each coil 44a, 44b may comprise a conductor 45 coiled around a central axis 46a, 46b to define a coil length 48 extending axially and a coil diameter 50 extending radially. The central axis 46a of one coil 44a may be radially spaced from, and parallel to, the central axis 46b or axes of the other coil 44b or coils 44.

In such an embodiment, each coil 44 may be matched to a corresponding core 40, coil form 42a, 42b, or some combination thereof. The two or more coils 44a, 44b may comprise one continuous winding. The winding may begin with a first coil 44a. When the turns of the first coil 44a are completed, the winding may begin the turns of a second coil 44b and so forth. In certain embodiments, the number of turns per coil 44 may be equal. In other embodiments, the number of turns may vary between coils 44.

The second coil 44b, as well as any other subsequent coils 44, may be wound in the same direction as the first coil 44b. Moreover, the various coils 44a, 44b may be connected in series. Accordingly, electrical currents induced in the coils

44*a*, 44*b* may flow in the same direction, reinforcing the total output current. The terminal ends 52*a*, 52*b* of the continuous winding may be attached to a circuit designed to process low frequency signals. Thus, antennas 38 in accordance with the present invention may provide the desired sensitivity in a compact envelope.

Figure 6:
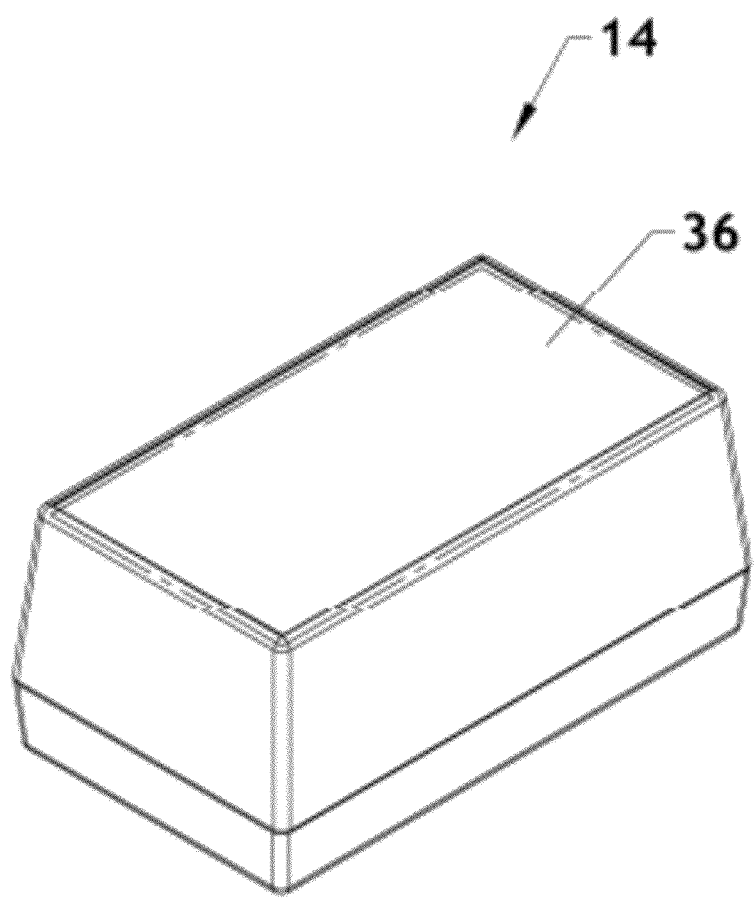
FIG. 6 is a perspective view of one embodiment of a marker in accordance with the present invention.
Figure 7:
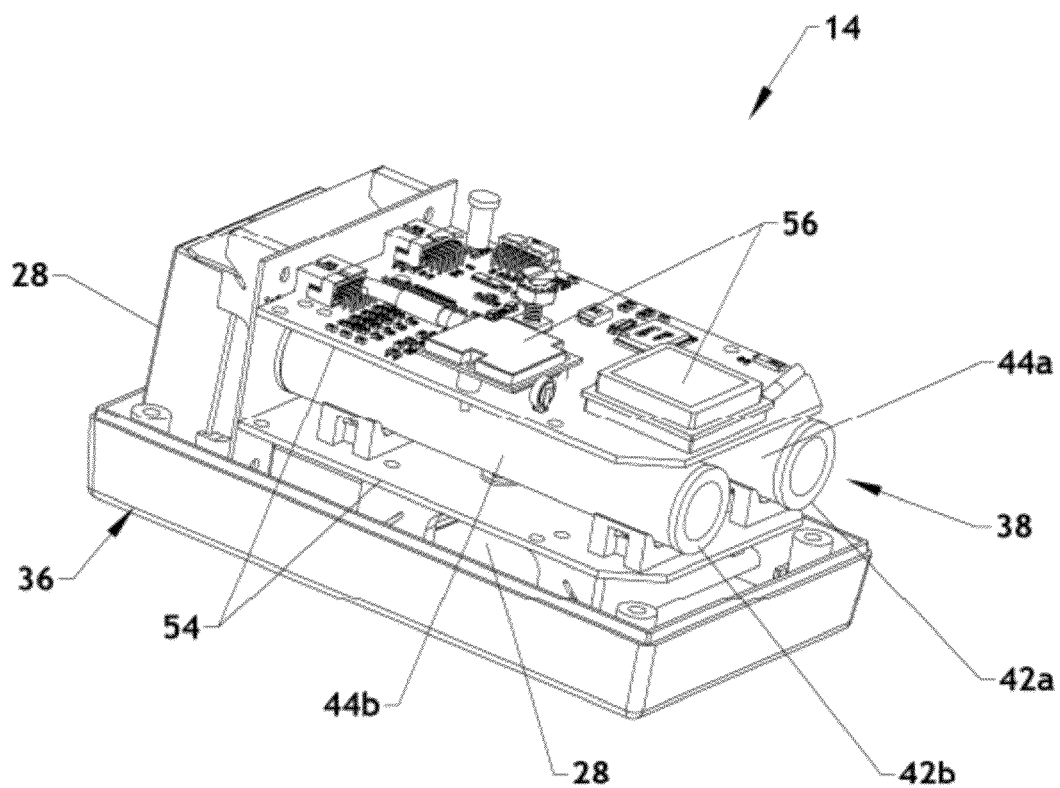
FIG. 7 is a perspective view of the marker of FIG. 6 with a portion of the housing removed to show the interior components thereof.

Referring to FIGS. 6 and 7, the compact envelope of an antenna 38 in accordance with the present invention may facilitate deployment of a corresponding marker 14. That is, markers 14 are often manually placed at various locations along a pipeline 16. This placement is often done by an installer traveling on foot. The compact size permits multiple markers 14 to be easily carried by foot (e.g., in an installer's backpack) to desired locations along a pipeline 16.

In selected embodiments, the various components of a marker 14 may be packed efficiently within a housing 36. For example, a marker 14 may be densely packed with one or more power supplies 28, one or more printed circuit boards 54, a multi-coil antenna 38, one or more GPS modules 56, etc.

Figure 8:
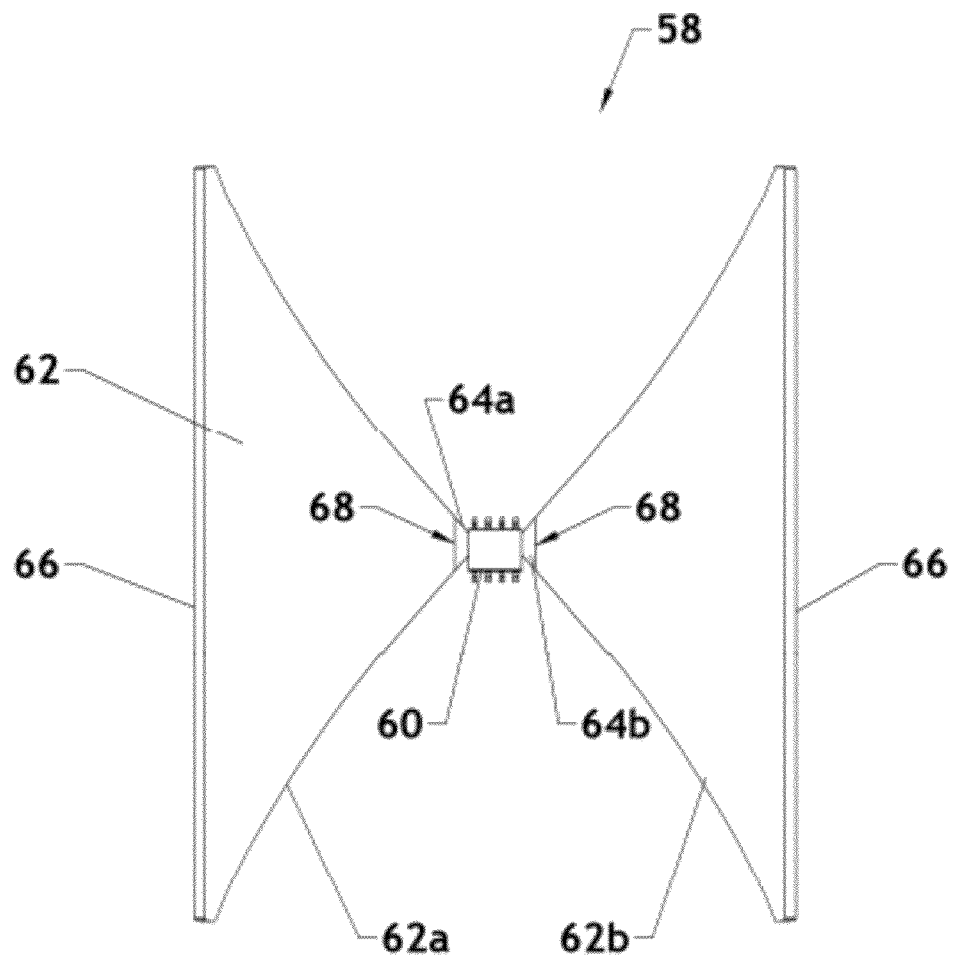
FIG. 8 is a top, plan view of one embodiment of a magnetic flux detection system comprising a flux sensor positioned between two flux concentrators in accordance with the present invention.
Figure 9:
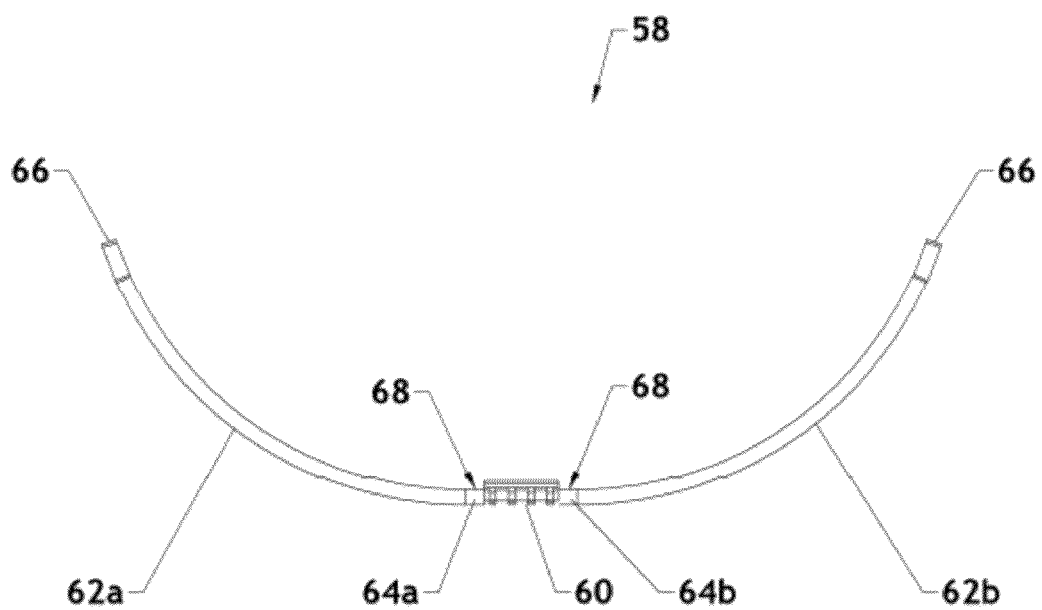
FIG. 9 is a side, elevation view of the flux detection system of FIG. 8.
Figure 10:
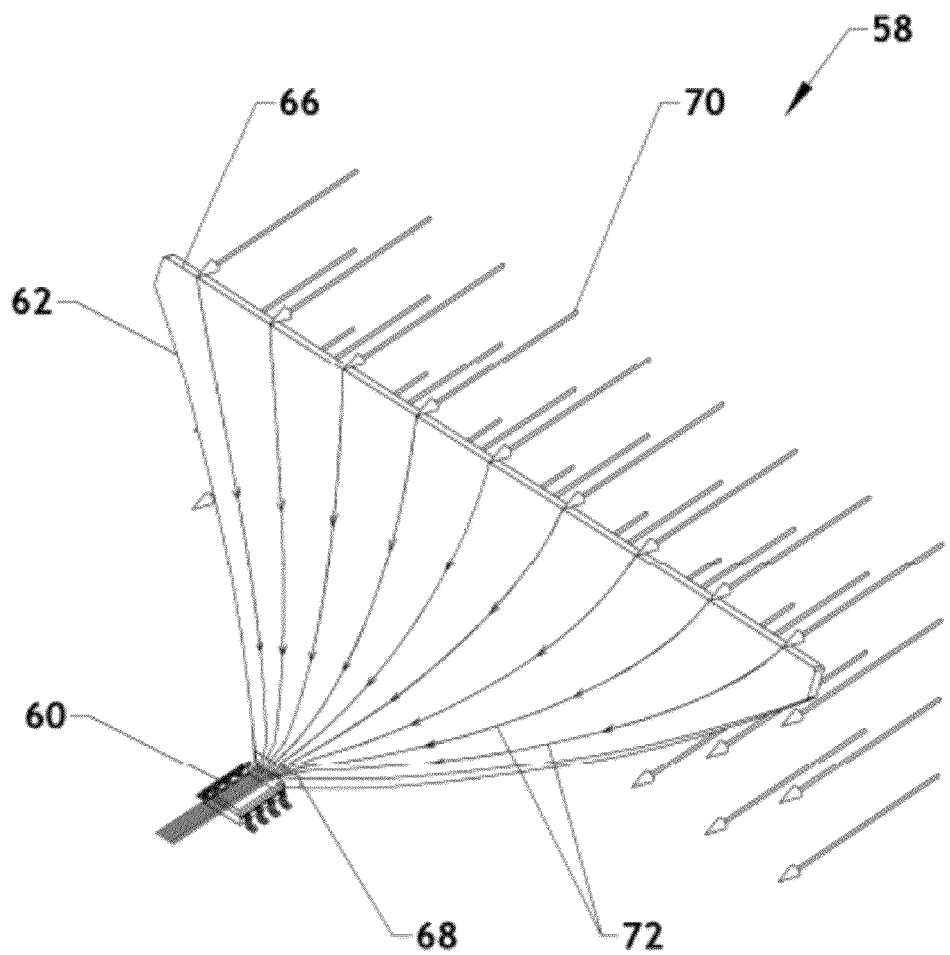
FIG. 10 is a partial perspective view of the flux detection system of FIG. 8.

Referring to FIGS. 8-10, in selected embodiments, a system 10 in accordance with the present invention may include one or more flux detection systems 58. A flux detection system 58 may include a flux sensor 60 and one or more flux concentrators 62 to strengthen the magnetic flux field delivered to the flux sensor 60. For example, in the illustrated embodiment, a first flux concentrator 62*a* strengthens the magnetic flux field delivered to the input 64*a* of a flux sensor 60. Flux passes through the sensor 60 and exits at point 64*b* where a second flux concentrator 62*b* provides continuity to the concentrated flux field and returns the concentrated field to the normal level in the ambient background field.

Accordingly, one flux concentrator 62*a* may fulfill the concentration role, while the other 62*b* guides the concentrated flux field through the flux sensor 60, receives the concentrated flux field, and distributes the flux field back to its original dimensions. When the orientation of the magnetic flux field or the flux detection system 58 changes, the roles of the respective flux concentrators 62 may change. That is, the second flux concentrator 62*b* may fulfill the concentration role, while the first concentrator 62*a* fulfills the guiding and distribution role.

A flux concentrator 62 in accordance with the present invention may be formed of a material with higher magnetic permeability than the surrounding matter (e.g., air). A flux concentrator 62 may have a relatively wide distal end 66 or edge 66 and a relatively narrow proximal end 68 or edge 68. A flux concentrator 62 may further include a gradual taper creating a smooth transition from the distal end 66 to the proximal end 68. In selected embodiments, a flux concentrator 62 may gradually curve as it extends away from the flux sensor 60. Thus, the taper from the wide, distal end 66 to the narrow, proximal end 68 may present a front to multiple orthogonal directions.

In operation, a flux concentrator 62 may present a front to an ambient flux field 70. Due to its higher magnetic permeability, a flux concentrator 62 may also create a shorter magnetic path. Accordingly, flux 72 may be routed in the concentrator 62 and concentrated at the narrow end 68, proximate a flux sensor 60. The flux sensor 60 may measure the strength of the concentrated magnetic field more readily than the strength of the lower level ambient field 70.

A flux concentrator 62 in accordance with the present invention may concentrate a three dimensional ambient flux field 70. A three dimensional ambient flux field 70 may have a two dimensional front. A flux concentrator 62 may collect the flux 72 from the front and decrease the vertical and horizontal dimensions thereof to the much smaller vertical and horizontal dimensions of an input 64 of an adjacent flux sensor 60. While the same total flux 72 may be present at both the distal end 66 and the proximal end 68 of a flux concentrator 62, the flux density may be much higher at the proximal end 68. This concentration of an ambient flux field 70 may be accomplished without regard to the orientation of the flux concentrator 62 or flux detection system 58 with respect to the ambient flux field 70. The flux detection system 58 simply concentrates flux density from the component of the flux field that presents a front to the flux concentrator 62.

Figure 11:
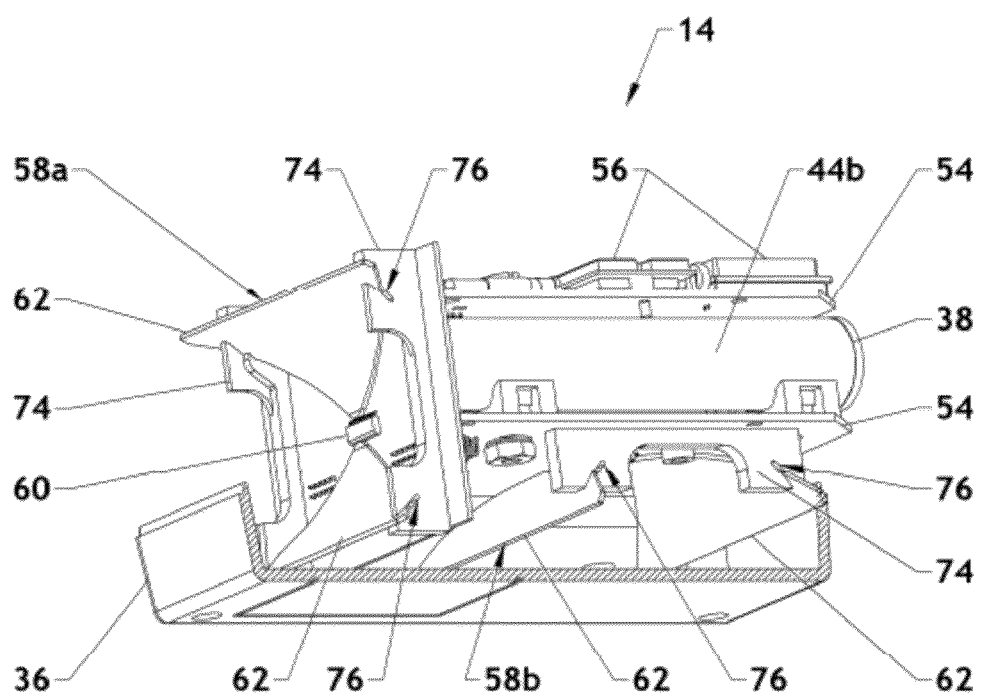
FIG. 11 is a perspective view of one embodiment of an above-ground marker with a portion of the housing removed to show multiple flux detection systems housed therein in accordance with the present invention.

Referring to FIG. 11, in-line tools 12 that use magnetic flux leakage to detect pipeline defects typically carry high strength magnets. These magnets generate a flux field 70 extending outside the pipeline 16 in which the in-line tool 12 is traveling. Accordingly, in selected embodiments in accordance with the present invention, the flux field 70 generated by an in-line tool 12 may be sensed by a marker 14 and used to locate the in-line tool 12 or sense the approach of the in-line tool 12 as it travels through a pipeline 16.

In selected embodiments, in-line tools 12 that do not normally carry magnets may have magnets added thereto to assist in locating the tools 12 as they travel through a pipeline 16. For example, magnets can be attached to cleaning pigs 12, in-line inspection tools 12 that do not use magnet flux leakage for defect detection, and the like. Accordingly, a wide variety of in-line tools 12 may be located using a marker 14 in accordance with the present invention.

In certain embodiments, a marker 14 in accordance with the present invention may include one or more flux detection systems 58. For example, in one embodiment, a marker 14 may include two flux detection systems 58*a*, 58*b* configured to sense the magnets of an in-line tool 12. The flux concentrators 62 of the one or more flux detection systems 58 may enable a marker 14 to locate an in-line tool 12 much more readily.

The magnetic field 70 generated by the magnets carried on an in-line tool 12 may have a general or primary direction with three dimensional components, namely an axial component extending axially along the pipeline 16, radial component extending radially with respect to the pipeline 16, and circumferential component extending circumferentially with respect to the pipeline 16. The presence of an in-line tool 12 may be detected using one or more of the axial, radial, or circumferential components of the magnetic field 70. In the illustrated embodiment, the marker 14 includes a first flux detection system 58*a* focusing on the radial component of the magnetic field 70 and a second flux detection system 58*b* focusing on the axial component of the magnetic field 70.

A flux detection system 58 may be secured within a marker 14 in any suitable manner. For example, in selected embodiments, a marker 14 may include a pair of parallel flanges 74 extending to engage a flux detection system 58. A flange 74 may extend along each side of the flux detection system 58. Slots 76 formed in the flanges 74 may provide locations for receiving corresponding flux concentrators 62. In certain embodiments, the flux concentrators 62 may be glued within the slots 76. Alternatively, the slots 76 may cooperate with other components (e.g., the housing 36 of the marker 14, the circuit board on which the flux sensor 60 is mounted, etc.) to effectively constrain the movement of the flux concentrators 58.

Figure 12:
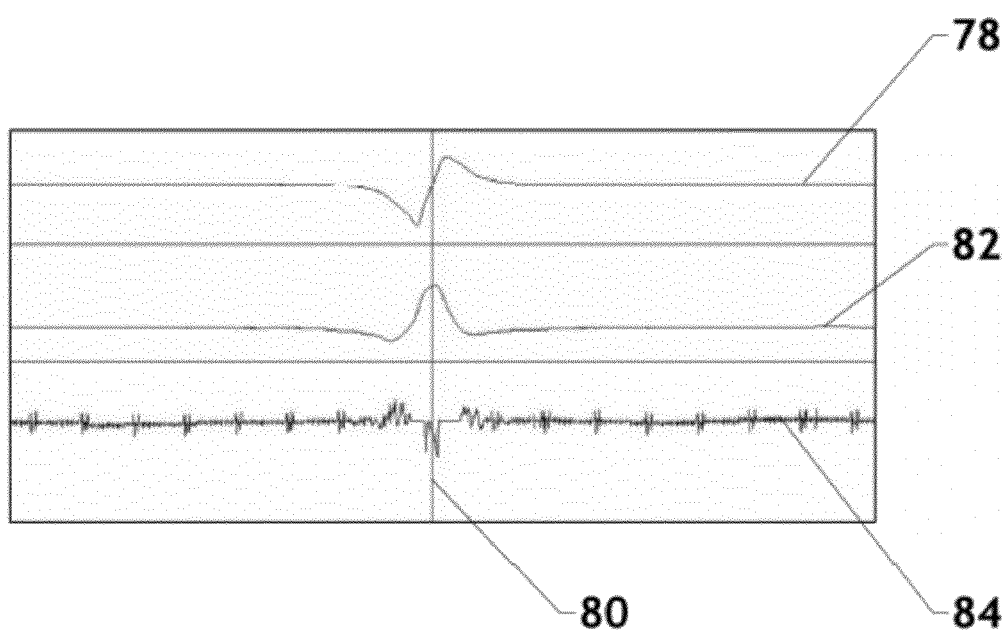
FIG. 12 is a graph plotting the various signals recorded by one embodiment of an above ground marker in accordance with the present invention.

Referring to FIG. 12, under normal circumstances, the radial component of the flux field 70 from a passing in-line tool 12 will pass through the vertical flux detection system 58*a*. The direction and amplitude of this component, as it is seen by the stationary marker 14, will vary and produce a recognizable signal 78 or trace 78. In selected embodiments, this trace 78 may have a zero value as the center 80 of the magnet field 70 passes directly by the marker 14. The trace 78 may also have maximum values of opposite sign on each side of the center 80.

Conversely, under normal circumstances, the axial component of the flux field 70 from a passing in-line tool 12 will pass through the horizontal flux detection system 58b. The direction and amplitude of this component, as it is seen by the stationary marker 14, will vary and produce a recognizable signal 82 or trace 82. In selected embodiments, this trace 82 may have a maximum peak as the center 80 of the magnet field 70 passes directly by the marker 14.

An in-line tool 12 may be detected by the presence of any component of the flux field 70. However, other electromagnetic phenomena exist that could produce a false indication of the presence of the in-line tool 12. Accordingly, in selected embodiments, a system 10 in accordance with the present invention may discriminate between the magnetic field 70 of an in-line tool 12 and some other electromagnetic phenomena by first searching a signal 78, 82 for the characteristic shape of the corresponding component of the magnetic field 70. The system 10 may further require that the signal 78, 82 have that characteristic shape before sending an indication that the in-line tool 12 has passed thereby.

For added accuracy, in certain embodiments, a system 10 may search multiple signals 78, 82 for the corresponding shapes. The system 10 may only send an indication that the in-line tool 12 has passed when those multiple signals all simultaneously display their corresponding characteristic shapes. In selected embodiments, these multiple signals 78, 82 may include the signal 84 received by an antenna 38 in accordance with the present invention. Accordingly, any combination of components of a magnetic field 70 and the signal 84 receive by an antenna 38 may be used to discriminate between signals coming from an in-line tool 12 passing thereby and those coming from other sources.

For example, like the signals 78, 82 derived from the magnetic field 70 of an in-line tool 12, the signal 84 or trace 84 received by an antenna 38 may also contain recognizable characteristics. These characteristics may be used to discriminate the passage of an in-line tool 12 from other phenomena. By using shape recognition and requiring multiple and simultaneous "witnesses" to the passage of an in-line tool 12, a marker 14 in accordance with the present invention may greatly improve the accuracy with which it detects in-line tools 12.

In selected embodiments, identification of signals 78, 82, 84 containing characteristic shapes, identification of times when the characteristic shapes occur simultaneously, and processing of the signal 84 received by the antenna 38 may all be handled by a processor 22 onboard the marker 14. In such embodiments, the marker 14 may include one or more buffers (e.g., memory 24) storing all signals 78, 82, 84 received by the marker 14 for a certain period of time. For example, the marker 14 may include a FIFO or first-in-first-out buffer. Accordingly, signal 78, 82, 84 may be captured for a period of time before a trigger occurs, allowing a section of time to be evaluated both before and after a center point 80.

The present invention may be embodied in other specific forms without departing from its spirit or essential characteristics. The described embodiments are to be considered in all respects only as illustrative, and not restrictive. The scope of the invention is, therefore, indicated by the appended claims, rather than by the foregoing description. All changes which come within the meaning and range of equivalency of the claims are to be embraced within their scope.

What is claimed and desired to be secured by United States Letters Patent is:

1. A marker comprising:
    a radio receiver having a coil antenna comprising at least two coils electrically connected in series;
    the radio receiver wherein each coil of the at least two coils comprises a conductor coiled around a central axis to define a coil length extending axially and a coil diameter extending radially;
    the radio receiver wherein the central axis of one coil of the at least two coils is radially spaced from and parallel to the central axes of all other coils of the at least two coils; and
    first and second flux detection systems, each comprising
        a flux sensor, a first flux concentrator positioned on one side of the flux concentrator, and a second flux concentrator positioned on the opposite side of the flux sensor,
        the first and second flux concentrators formed of magnetically permeable material,
        the first and second flux concentrators each having a proximal edge and a distal edge, the distal edge being longer than the proximal edge,
        the first and second flux concentrators each curving and tapering as it extends from the distal edge to the proximal edge, and
        the first and second flux concentrators each being positioned with respect to the flux sensor such that the proximal edge is positioned directly adjacent the flux sensor.

2. The marker of claim 1, further comprising a computer system comprising a processor operably connected to at least one memory device, the computer system configured to record and process first and second signals output by the first and second flux detection systems, respectively.

3. The marker of claim 2, wherein the computer system is further configured to record and process a radio signal output by the coil antenna.

4. The marker of claim 3, wherein the computer system is further configured to search the first and second signals for respective first and second characteristics indicative of an in-line tool passing by the marker.

5. The marker of claim 4, wherein the computer system is further configured to record a passage thereby of the in-line tool exclusively when the first and second signals respectively and simultaneously display the first and second characteristics.

6. The marker of claim 5, wherein the computer system is further configured to search the radio signal for a third characteristic indicative of the in-line tool passing by the marker.

7. The marker of claim 6, wherein the computer system is further configured to record a passage thereby of the in-line tool exclusively when the first signal, second signal, and radio signal respectively and simultaneously display the first, second, and third characteristics.

8. A marker comprising:
    a power source;
    a receiver for a global positioning system;
    a radio receiver having a coil antenna comprising at least two coils electrically connected in series;
    the radio receiver wherein each coil of the at least two coils comprises a conductor coiled around a central axis to define a coil length extending axially and a coil diameter extending radially;
    the radio receiver wherein the central axis of one coil of the at least two coils is radially spaced from and parallel to the central axes of all other coils of the at least two coils;

a flux detection system comprising
- a flux sensor, a first flux concentrator positioned on one side of the flux concentrator, and a second flux concentrator positioned on the opposite side of the flux sensor,
- the first and second flux concentrators formed of magnetically permeable material,
- the first and second flux concentrators each having a proximal edge and a distal edge, the distal edge being longer than the proximal edge,
- the first and second flux concentrators each curving and tapering as it extends from the distal edge to the proximal edge, and
- the first and second flux concentrators each being positioned with respect to the flux sensor such that the proximal edge is positioned directly adjacent the flux sensor; and a housing containing the power source, the receiver for the global positioning system, the flux detection system, and the radio receiver.

* * * * *